(12) United States Patent
Matheny

(10) Patent No.: US 10,993,802 B2
(45) Date of Patent: *May 4, 2021

(54) SYSTEMS, APPARATUS AND METHODS FOR SEALING PERIVALVULAR LEAKS

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 677 days.

This patent is subject to a terminal disclaimer.

(21) Appl. No.: 15/835,714

(22) Filed: Dec. 8, 2017

(65) Prior Publication Data

US 2018/0104050 A1 Apr. 19, 2018

Related U.S. Application Data

(63) Continuation-in-part of application No. 15/652,767, filed on Jul. 18, 2017, now Pat. No. 9,867,696, and a continuation of application No. 14/483,557, filed on Sep. 11, 2014, now Pat. No. 9,737,399.

(60) Provisional application No. 61/876,540, filed on Sep. 11, 2013.

(51) Int. Cl.
*A61F 2/24* (2006.01)

(52) U.S. Cl.
CPC .......... *A61F 2/2412* (2013.01); *A61F 2/2463* (2013.01); *A61F 2250/0069* (2013.01)

(58) Field of Classification Search
CPC .................. A61F 2/2412; A61F 2/2463; A61F 2250/0069; A61F 2/2418; A61F 2/2436; A61F 2/2439; A61F 2/24; A61F 2/2487; A61F 2/243; A61F 2/246

See application file for complete search history.

(56) References Cited

U.S. PATENT DOCUMENTS

| 8,778,012 | B2 * | 7/2014 | Matheny | A61L 27/3633 623/1.36 |
|---|---|---|---|---|
| 9,533,072 | B2 * | 1/2017 | Matheny | A61L 27/3834 |
| 2005/0013870 | A1 * | 1/2005 | Freyman | A61L 27/3633 424/520 |
| 2005/0096736 | A1 * | 5/2005 | Osse | A61F 2/2418 623/1.26 |
| 2007/0014868 | A1 * | 1/2007 | Matheny | A61K 35/38 424/551 |

(Continued)

FOREIGN PATENT DOCUMENTS

WO WO-2011031827 A2 * 3/2011 ......... A61L 27/3683

*Primary Examiner* — Jerrah Edwards
*Assistant Examiner* — Rokhaya Diop
(74) *Attorney, Agent, or Firm* — Francis Law Group

(57) ABSTRACT

A biocompatible and biodegradable construct having a base expandable member and an integral, internal support structure. The support structure is preferably formed from poly (glycerol sebacate) (PGS) or a magnesium alloy. The base member is preferably formed from acellular extracellular matrix (ECM) derived from small intestine submucosa (SIS) tissue that exhibits a flexible, porous, sponge-like structure adapted to expand upon absorption of a bodily fluid, wherein the construct seals a perivalvular leak when disposed proximate thereto.

6 Claims, 6 Drawing Sheets

(56) References Cited

U.S. PATENT DOCUMENTS

| | | | | |
|---|---|---|---|---|
| 2007/0027535 | A1* | 2/2007 | Purdy, Jr. | A61L 27/18 623/2.18 |
| 2007/0162103 | A1* | 7/2007 | Case | A61F 2/2412 623/1.13 |
| 2012/0302499 | A1* | 11/2012 | Matheny | A61L 27/3633 514/8.9 |
| 2013/0030521 | A1* | 1/2013 | Nitzan | A61B 17/0057 623/2.13 |
| 2014/0288642 | A1* | 9/2014 | Yoshida | A61F 2/2412 623/2.17 |

* cited by examiner

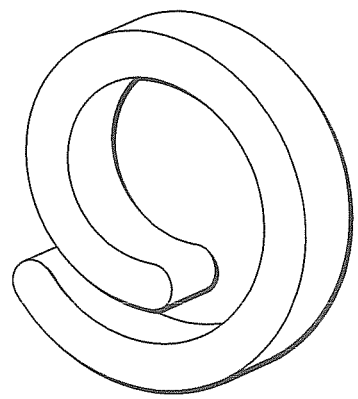 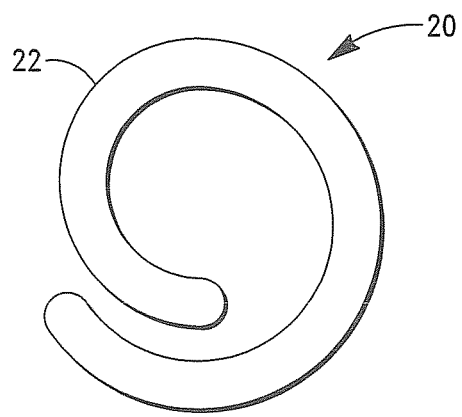
*FIG. 2A*  *FIG. 2B*
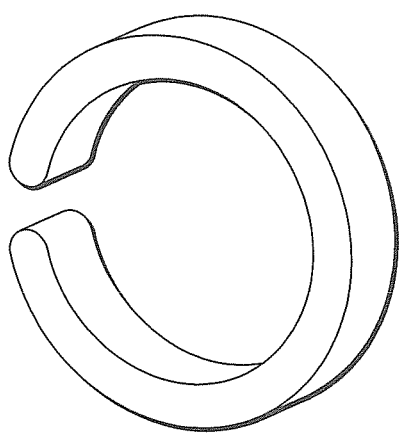 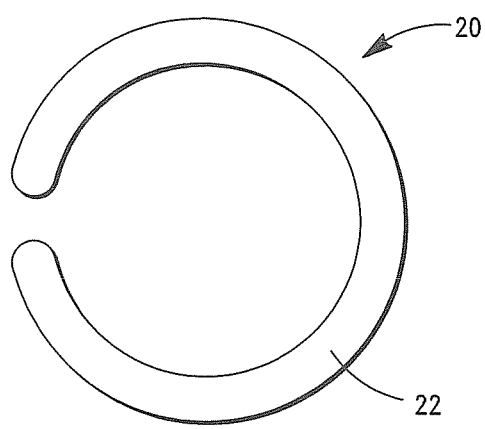
*FIG. 3A*  *FIG. 3B*

SYSTEMS, APPARATUS AND METHODS FOR SEALING PERIVALVULAR LEAKS

CROSS-REFERENCE TO RELATED APPLICATIONS

This application is a continuation-in-part of U.S. application Ser. No. 15/652,767, filed on Jul. 18, 2017, which is a continuation of U.S. application Ser. No. 14/483,557, filed on Sep. 11, 2014, now U.S. Pat. No. 9,737,399, which claims priority to U.S. Provisional Application No. 61/876,540, filed on Sep. 11, 2013.

FIELD OF THE INVENTION

The present invention generally relates to replacement prosthetic valves. More particularly, the present invention relates to an apparatus and method for sealing perivalvular leaks; particularly, perivalvular leaks encountered during or after a cardiovascular valve replacement.

BACKGROUND OF THE INVENTION

As is well known in the art, the human heart has four valves that control blood flow circulating through the human body. On the left side of the heart is the mitral valve, located between the left atrium and the left ventricle, and the aortic valve, located between the left ventricle and the aorta. Both of these valves direct oxygenated blood from the lungs into the aorta for distribution through the body.

The tricuspid valve, located between the right atrium and the right ventricle, and the pulmonary valve, located between the right ventricle and the pulmonary artery, however, are situated on the right side of the heart and direct deoxygenated blood from the body to the lungs.

The peripheral venous system also includes a number of valves that prevent retrograde blood flow. By preventing retrograde blood flow, the valves found throughout the venous system assist the flow of blood through the veins and returning to the heart.

Normally, the mitral valve has two leaflets and the tricuspid valve has at least two, preferably, three leaflets. The aortic and pulmonary valves, however, have normally at least two, preferably three leaflets, also often referred to as "cusps" because of their half-moon like appearance.

Venous valves are usually of the bicuspid type, with each cusp or leaflet forming a reservoir for blood, which, under pressure, forces the free edges of the cusps together to permit mostly antegrade blood flow to the heart. As discussed in detail below, since a majority of venous blood flow is against gravity while a person is standing, incompetent or destroyed venous valves can cause significant medical problems in the legs, ankles, and feet.

Valve diseases are typically classified into two major categories; stenosis and insufficiency. In the case of a stenosis, the native valve does not open properly, whereby insufficiency represents the opposite effect showing deficient closing properties.

Insufficiency of the inlet (atrioventricular) tricuspid valve to the right ventricle of the heart results in regurgitation of blood back into the right atrium, which, serving to receive blood flow returning in the veins from the entire body, then results, in turn, in suffusion and swelling (edema) of all the organs, most notably in the abdomen and extremities, insufficient forward conduction of blood flow from the right ventricle into the lungs causing compromise of pulmonary function, and ultimately pump failure of the right heart. Collectively these conditions are termed right heart failure, a condition that leads to incapacity and possibly to death if progressive and uncorrected.

Insufficiency of vein function due to the incompetence or destruction of peripheral venous valves leads to acute then chronic swelling of the veins and their dependent lymphatics and tissues. This condition can affect the deep veins of the body; commonly, the lower extremities or pelvis, or the superficial veins of the lower extremities in particular, leading to progressive expansion of the veins and further valvular incompetence, a condition known as varicose veins.

Medical conditions like high blood pressure, inflammatory and infectious processes often lead to stenosis and insufficiency. Treatment of heart valve dysfunctions typically include reparation of the diseased heart valve with preservation of the patient's own valve or replacement of the valve with a mechanical or bioprosthetic "tissue" valve, i.e. a prosthetic heart valve. Particularly for aortic heart valves, however, it is frequently necessary to introduce a heart valve replacement.

Various prosthetic heart valves have thus been developed for replacement of natural diseased or defective valves. Illustrative are the bioprosthetic "tissue" valves disclosed in Applicant's Co-Pending application Ser. No. 13/560,573.

The implantation of a prosthetic valve, including mechanical valves and bioprosthetic valves, requires a great deal of skill and concentration given the delicate nature of the native cardiovascular tissue and the spatial constraints of the surgical field. It is also critical to achieve a secure and reliable attachment of the valve to host cardiovascular tissue.

Various structures and means have thus been developed to provide a secure and reliable attachment of a prosthetic valve to host cardiovascular tissue. Most surgical techniques comprise suturing the ends of the valve to the annulus of the cardiovascular vessel.

There are numerous drawbacks and disadvantages associated with suturing a valve to host tissue. A major disadvantage is the high risk of a perivalvular leak.

In U.S. application Ser. No. 13/560,573 the tissue valve includes a sewing ring that can be employed to suture the ends of the valve to the annulus of the cardiovascular vessel. Although the use of a sewing ring to secure the valve to a cardiovascular vessel can be, and most times is, highly effective, perivalvular leaks are often encountered during or after a cardiovascular valve replacement.

Referring to FIG. 1A, a typical perivalvular leak occurs when there is a gap 18 between the valve 14a and vessel 16 (or valve annulus).

Perivalvular leaks can also occur during or after a cardiovascular valve when the replacement valve is placed over native and, often, calcified valve leaflets, which is a common procedure.

As illustrated in FIG. 1B, the native leaflets 12 are, thus, wedged between the replacement valve 14a and the vessel 16, which can, and often will, result in gaps 18 between the valve 14a and vessel 16 that can lead to perivalvular leaks.

There is thus a need to provide an apparatus and method for sealing perivalvular leaks; particularly, leaks encountered during or after a cardiovascular valve replacement.

It is therefore an object of the present invention to provide an apparatus and method for sealing perivalvular leaks; particularly, leaks encountered during or after a cardiovascular valve replacement.

It is another object of the present invention to provide an apparatus for sealing perivalvular leaks that induces remodeling and regeneration of cardiovascular tissue.

SUMMARY OF THE INVENTION

The present invention is directed to systems, apparatus and methods for sealing perivalvular leaks; particularly, perivalvular leaks encountered during or after a cardiovascular valve replacement.

In a preferred embodiment, the perivalvular leak sealing apparatus comprises a biocompatible, expandable construct that is adapted to expand upon exposure to and absorption of a bodily fluid.

In some embodiments of the invention, the expandable construct comprises a remodelable construct that is capable of transitioning from a pre-deployment configuration, wherein the expandable remodelable member is capable of being positioned proximate a perivalvular leak, to a post-deployment expanded configuration when the expandable remodelable construct is exposed to and absorbs a bodily fluid, wherein the expandable remodelable construct seals the perivalvular leak.

In some embodiments of the invention, the expandable remodelable construct comprises acellular extracellular matrix (ECM) derived from mammalian small intestine submucosa tissue.

In a preferred embodiment of the invention, the acellular ECM comprises a flexible, porous, e.g., sponge-like, structure.

In some embodiments of the invention, the acellular ECM (and/or ECM expandable member formed therefrom) comprises at least one supplemental biologically active agent (or composition).

In some embodiments of the invention, the biologically active agent comprises a hemostatic agent or composition.

In some embodiments, the hemostatic agent is selected from the group comprising thrombin, fibrinogen, fibronectin, plasminogen, aprotinin, α-2-antiplasmin, α-2 macroglobulin, α-1-antitrypsin, epsilon-aminocaproic acid, tranexamic acid, and a plasmin activator inhibitor, e.g., PAI-1 and PAI-2.

In some embodiments of the invention, the biologically active agent comprises a statin, i.e. a HMG-CoA reductase inhibitor, selected from the group comprising atorvastatin, cerivastatin, fluvastatin, lovastatin, mevastatin, pitavastatin, pravastatin, rosuvastatin, and simvastatin.

In some embodiments of the invention, the biologically active agent comprises a growth factor selected from the group comprising fibroblast growth factor-2 (FGF-2), transforming growth factor beta (TGF-β) and vascular epithelial growth factor (VEGF).

In some embodiments of the invention, the acellular ECM (and/or ECM expandable member formed therefrom) comprises a pharmacological agent (or composition), i.e. an agent or composition that is capable of producing a desired biological effect in vivo, e.g., stimulation or suppression of apoptosis, stimulation or suppression of an immune response, etc.

According to the invention, the pharmacological agent or composition can comprise, without limitation, antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the expandable remodelable construct further comprises an integral, internal support (or anchoring) structure.

In some embodiments, the support structure comprises magnesium or a magnesium alloy.

In some embodiments, the support structure comprises poly(glycerol sebacate) (PGS).

In some embodiments, the support structure comprises a microneedle support structure comprising a plurality of biodegradable microneedles or barbs that are adapted to engage cardiovascular tissue.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 2A is a perspective view of one embodiment of a perivalvular leak sealing apparatus in a pre-deployment configuration, in accordance with the invention;

FIG. 2B is a front plan view of the perivalvular leak sealing apparatus shown in FIG. 2A in a pre-deployment configuration, in accordance with the invention;

FIG. 3A is a perspective view of the perivalvular leak sealing apparatus shown in FIG. 2A in one embodiment of a post-deployment configuration, in accordance with the invention;

FIG. 3B is a front plan view of the perivalvular leak sealing apparatus shown in FIG. 2A in one embodiment of a post-deployment configuration, in accordance with the invention;

DETAILED DESCRIPTION OF THE PREFERRED EMBODIMENT

Figure 1A:
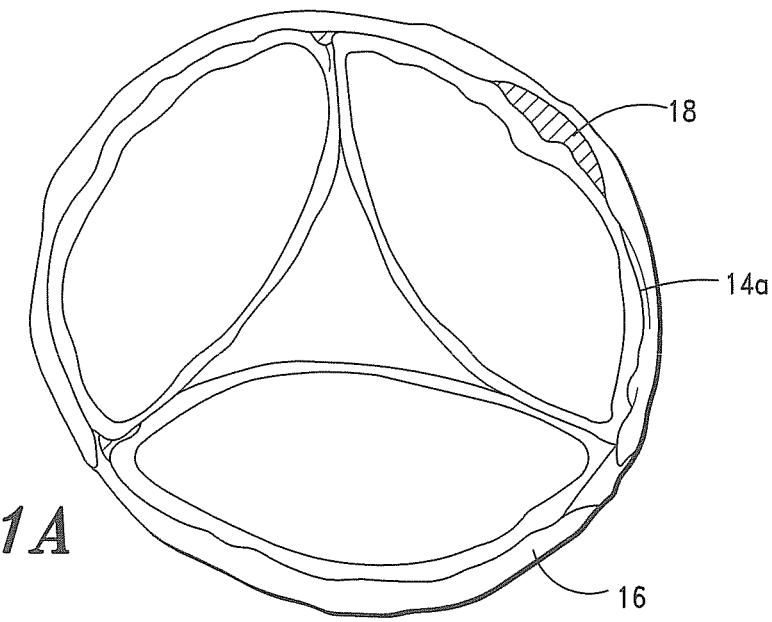
FIGS. 1A and 1B are illustrations of a replacement valve disposed in a cardiovascular vessel, showing gaps and, hence, perivalvular leak regions therebetween.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM" and "ECM material" are used interchangeably herein, and mean and include a collagen-rich substance that is found in between cells in mammalian tissue, and any material processed therefrom, such as, without limitation, decellularized ECM.

According to the invention, the ECM can be derived from a variety of mammalian tissue sources, including, without limitation, small intestine submucosa (SIS), urinary bladder submucosa (UBS), stomach submucosa (SS), central nervous system tissue, dermal tissue, subcutaneous tissue, gastrointestinal tissue, i.e. large and small intestine tissue, tissue surrounding growing bone, placental tissue, omentum tissue, cardiac tissue, e.g., pericardium and/or myocardium tissue, kidney tissue, pancreas tissue, lung tissue, and combinations thereof. The ECM can also comprise collagen from mammalian sources.

The terms "urinary bladder submucosa (UBS)", "small intestine submucosa (SIS)" and "stomach submucosa (SS)" also mean and include any UBS and/or SIS and/or SS tissue that includes the tunica mucosa (which includes the transitional epithelial layer and the tunica propria), submucosal layer, one or more layers of muscularis, and adventitia (a loose connective tissue layer) associated therewith.

The ECM can also be derived from epithelium of mesodermal origin, i.e. mesothelial tissue.

The ECM can additionally be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM can also be derived from other sources, including, without limitation, collagen from plant sources and synthesized extracellular matrices, i.e. cell cultures.

The terms "sponge" and "sponge-like configuration" are used interchangeably herein, and mean and include an elastic, porous structure that is capable of absorbing a bodily fluid when in contact therewith and expanding, i.e. increasing in mass and volume, thereafter.

The term "expandable" as used in conjunction with a base construct of a perivalvular leak sealing apparatus or system of the invention means and includes a member or construct (with and without an integral support structure) that is capable of transitioning from a pre-deployment configuration to an expanded post-deployment configuration in a body or structure associated therewith when exposed to a bodily fluid.

The term "bodily fluid" means and includes any aqueous fluid contained in and/or produced by a mammalian body, including, without limitation, blood, water, lymphatic fluid, saliva, plasma, digestive fluids, bile, urine and amniotic fluid.

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition", as used herein, thus mean and include a hemostatic agent or composition, including, without limitation, thrombin, fibrinogen, fibronectin, plasminogen, aprotinin, $\alpha$-2-antiplasmin, $\alpha$-2 macroglobulin, $\alpha$-1-antitrypsin, epsilon-aminocaproic acid, tranexamic acid, and a plasmin activator inhibitor, e.g., PAI-1 and PAI-2.

The terms "biologically active agent" and "biologically active composition" also mean and include, without limitation, the following growth factors: platelet derived growth factor (PDGF), epidermal growth factor (EGF), transforming growth factor $\alpha$ (TGF-$\alpha$), transforming growth factor beta (TGF-$\beta$), fibroblast growth factor-2 (FGF-2), vascular epithelial growth factor (VEGF), hepatocyte growth factor (HGF), insulin-like growth factor (IGF), nerve growth factor (NGF), platelet derived growth factor (PDGF), tumor necrosis factor-$\alpha$ (TNA-$\alpha$), and placental growth factor (PLGF).

The terms "biologically active agent" and "biologically active composition" also mean and include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogeneic cells, allogeneic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (derrnatan sulfate), chondroitin sulfate A, heparin sulfates, hyaluronic acids, fibronectins, tenascins, elastins, fibrillins, laminins, nidogen/enactins, fibulin I, fibulin II, integrins, transmembrane molecules, thrombospondins, osteopontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "pharmacological agent", "active agent", "drug" and "active agent formulation" can further include one or more classes of cytotoxic anti-neoplastic agents or chemotherapy agents, including, without limitation, alkylating agents, cisplatin, carboplatin, oxaliplatin, mechlorethamine, cyclophosphamide, chlorambucil, and ifosfamide. Chemotherapy agents can also include, without limitation, antimetabolites, such as purine analogues, pyrimidine analogues and antifolates, plant alkaloids, such as vincristine, vinblastine, vinorelbine, vindesine, podophyllotoxin, etoposide and teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibody treatments, such as abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, a amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endiysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "therapeutically effective", as used herein, means that the amount of the "pharmacological agent" and/or "biologically active agent" and/or "pharmacological composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "abate", "prevent" and "preventing" are used interchangeably herein, and mean and include reducing the frequency or severity of a condition or disorder. The term does not require an absolute preclusion of the condition or disorder.

The terms "treat" and "treatment" are used interchangeably herein, and mean and include medical management of a patient with the intent to cure, ameliorate, stabilize, or prevent a disease, pathological condition or disorder. The terms include "active treatment", i.e. treatment directed specifically toward the improvement of a disease, pathological condition or disorder, and "causal treatment", i.e. treatment directed toward removal of the cause of the associated disease, pathological condition or disorder.

The terms "treat" and "treatment" further include "palliative treatment", i.e. treatment designed for the relief of symptoms rather than the curing of the disease, pathological condition or disorder, "preventative treatment", i.e. treatment directed to minimizing or partially or completely inhibiting the development of the associated disease, pathological condition or disorder, and "supportive treatment", i.e. treatment employed to supplement another specific therapy directed toward the improvement of the associated disease, pathological condition or disorder.

The terms "prosthetic valve" and "valve" are used interchangeably herein, and mean and include a valve construct that is configured to replace a native cardiovascular valve, such as the valve constructs disclosed in U.S. Pat. Nos. 8,696,744, 7,998,196, 9,044,319 and 8,709,076, and Co-pending U.S. application Ser. Nos. 13/804,683 and 13/480,347, which are incorporated by reference herein.

The terms "delivery" and "administration" are used interchangeably herein, and mean and include placing a perivalvular leak sealing apparatus or system of the invention in an internal region of a cardiovascular valve through any method appropriate to deliver the perivalvular leak sealing apparatus, and in a space or gap between a prosthetic valve and cardiovascular vessel or structure.

The term "supplemental" and variations of the term, such as "augmented", as used in connection with a "biologically active agent or composition", means and includes the introduction of additional non-native agents, e.g., a statin, and native agents e.g., fibroblast growth factor-2 (FGF-2) to ECM (and/or an expandable ECM construct or member formed therefrom).

The term "comprise" and variations of the term, such as "comprising" and "comprises," means "including, but not limited to" and is not intended to exclude, for example, other additives, components, integers or steps.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to systems, apparatus and methods for sealing perivalvular leaks; particularly, perivalvular leaks encountered during or after a cardiovascular valve replacement.

Although the invention is primarily directed to systems, apparatus and methods for sealing perivalvular leaks, it is to be understood that the present invention is not limited to solely sealing perivalvular leaks. Indeed, as will be readily apparent to one having ordinary skill in the art, the invention disclosed herein can also be readily adapted and, hence, employed to seal leaks between grafts and biological tissue and structures associated therewith. For purposes herein, the terms "cardiovascular tissue" and "cardiovascular structures" thus include and, hence, are deemed equivalent to "biological tissue" and "biological structures."

In a preferred embodiment, the perivalvular leak sealing apparatus comprises a biocompatible, expandable construct (also referred to herein as "an expandable base construct") that is adapted to expand upon exposure to and absorption of a bodily fluid.

In some embodiments of the invention, the expandable construct comprises a remodelable (or bioremodelable) construct that is capable of transitioning from a pre-deployment configuration, wherein the expandable remodelable construct is capable of being positioned proximate a perivalvular leak, to a post-deployment expanded configuration when the expandable remodelable construct is exposed to and absorbs a bodily fluid, wherein the expandable remodelable construct expands and seals the perivalvular leak.

In some embodiments of the invention, the expandable remodelable construct comprises extracellular matrix (ECM) derived from a mammalian tissue source.

According to the invention, the ECM can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427, now U.S. Pat. No. 8,980,296; which are incorporated by reference herein in their entirety.

Suitable mammalian tissue sources include, without limitation, small intestine submucosa (SIS), urinary bladder submucosa (UBS), stomach submucosa (SS), central nervous system tissue, dermal tissue, subcutaneous tissue, gastrointestinal tissue, i.e. large and small intestine tissue, tissue surrounding growing bone, placental tissue, omentum tissue, cardiac tissue, e.g., pericardium and/or myocardium tissue, kidney tissue, pancreas tissue, lung tissue, and combinations thereof. The ECM can also comprise collagen from mammalian sources.

The ECM can also be derived from epithelium of mesodermal origin, i.e. mesothelial tissue, as well as the basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

In a preferred embodiment of the invention, the ECM comprises acellular ECM.

In a preferred embodiment, the acellular ECM is derived from SIS tissue.

According to the invention, the ECM can be decellularized by various conventional processes, such as the processes disclosed in Crapo, et al., *An Overview of Tissue and Whole Organ Decellularization Processes*, Biomaterials, vol. 32(12), pp. 3233-3243 (2011), which is incorporated by reference herein.

As one having ordinary skill in the art will readily recognize and appreciate, most conventional ECM decellularization processes, including the processes disclosed in Crapo, et al., do not include subjecting ECM to an alkaline agent or composition due to the adverse effects on the ECM.

Indeed, as is well established in the art, subjecting ECM to a decellularization process employing an alkaline agent or composition will render the ECM substantially devoid of seminal growth factors, glycoproteins, glycosaminoglycans, proteoglycans, nucleic acids, and lipids. ECM subjected to a decellularization process employing an alkaline agent or composition will thus have a substantially limited capacity to remodel and induce remodeling and regeneration of new cardiovascular tissue, when delivered to damaged cardiovascular tissue.

Thus, in accordance with some embodiments of the invention, the ECM is decellularized by subjecting the tissue to incubation in 0.005-10 vol. % of a decellularization agent in a conventional solute solution for a period of time in the range of 0.1-168 hours.

In some embodiments, the decellularization agent comprises a detergent including, without limitation, deoxycholic acid, sodium dodecyl sulfate (SDS), triton X-100 and 3-[(3-cholamidopropyl)dimethylammonio]-1-propanesulfonate (CHAPS).

In some embodiments, the decellularization agent comprises an oxidizing agent including, without limitation, peracetic acid (PAA), hydrogen peroxide ($H_2O_2$), acetic acid (AcA), trifluoroacetic acid (TFA), and mixtures thereof.

In some embodiments, the solute solution comprises distilled water. In some embodiments, the solute solution comprises a buffer solution, such as 5 mM EDTA in Dulbecco's phosphate buffered saline (DPBS).

In some embodiments, the ECM is decellularized by subjecting the tissue to incubation in 0.5-1.0 vol. % deoxycholic acid for a period of time in the range of approximately 24-48 hours.

In some embodiments, the ECM is decellularized by subjecting the tissue to incubation in 0.1-0.2 vol. % peracetic acid for a period of time in the range of approximately 1-2 hours.

In some embodiments, the combination of the decellularization agent and the solute solution provide a decellularization solution that comprises a pH in the range of 0-14.

In some embodiments, the decellularization solution preferably comprises an acidic to neutral pH, i.e. non-alkaline pH, in the range of 5.5-7.5.

In some embodiments of the invention, the ECM is decellularized via a process disclosed in Co-Pending PCT Application No. PCT/US12/039413 and Co-Pending U.S. application Ser. No. 13/480,140, now U.S. Pat. No. 8,877,224; which are incorporated by reference herein in their entirety.

In a preferred embodiment, the ECM subjected to one of the aforementioned decellularization processes, i.e. acellular ECM, exhibits a flexible, porous, e.g., sponge-like, expandable structure.

According to the invention, the acellular ECM (and, hence, expandable ECM members formed therefrom) is capable of remodeling and inducing remodeling and regeneration of new cardiovascular tissue, when delivered to damaged cardiovascular tissue.

Thus, in some embodiments of the invention, the perivalvular leak sealing apparatus comprises a two-stage perivalvular leak sealing structure comprising a physiomechanical leak abatement component and a biological leak abatement component, the two-stage leak abatement structure comprising an expandable, remodelable construct comprising acellular ECM derived from a mammalian tissue source, the acellular ECM and, hence, remodelable construct formed therewith, comprising a flexible, porous structure adapted to expand upon exposure to and absorption of a bodily fluid, wherein, when the two-stage perivalvular leak sealing structure is disposed proximate a perivalvular leak, such as a gap between a prosthetic tissue valve and cardiovascular structure, and absorbs a bodily fluid, the remodelable construct expands, is positioned in intimate contact with cardiovascular tissue proximate the perivalvular leak, and abates the perivalvular leak during a first leak sealing stage (i.e. a physiomechanical leak abatement component), and after a first period of time the remodelable construct remodels and induces remodeling of the cardiovascular tissue and regeneration of new cardiovascular tissue proximate the perivalvular leak, wherein the remodelable construct further abates the perivalvular leak during a second sealing stage (i.e. a biological leak abatement component).

According to the invention, the acellular ECM can be formed into a particulate, as described in U.S. Pat. Nos. 5,275,826, 6,579,538 and 6,933,326, and Co-Pending application Ser. No. 13/573,569, now U.S. Pat. No. 9,072,816; which are incorporated by reference herein in their entirety, to form a sponge-like, expandable ECM structure of the invention.

In some embodiments of the invention, the ECM is processed to provide a foam and chemically crosslinking the foam to form an expandable member, such as disclosed in U.S. application Ser. No. 12/488,974, filed on Jun. 22, 2009, which is incorporated by reference herein.

In some embodiments of the invention, the ECM is subjected to processing comprising subjecting the ECM to an alkaline solution and, optionally, a lipid removal agent, such as disclosed in U.S. application Ser. No. 14/591,100, filed on Jan. 7, 2015, which is also incorporated by reference herein.

In some embodiments of the invention, the ECM (and/or an expandable ECM member formed therefrom) comprises at least one supplemental, e.g., exogenously added, biologically active agent (or composition), i.e. an agent or composition that induces or modulates a physiological or biological process, or cellular activity, e.g., hemostatic activity, cell proliferation, and/or growth and/or regeneration of tissue.

In some embodiments of the invention, the biologically active agent comprises a hemostatic agent or composition.

In some embodiments, the hemostatic agent is selected from the group comprising thrombin, fibrinogen, fibronectin, plasminogen, aprotinin, $\alpha$-2-antiplasmin, $\alpha$-2 macroglobulin, $\alpha$-1-antitrypsin, epsilon-aminocaproic acid, tranexamic acid, and a plasmin activator inhibitor, e.g., PAI-1 and PAI-2.

In some embodiments, the hemostatic agent comprises thrombin.

In some embodiments, the hemostatic agent comprises fibrinogen.

In some embodiments of the invention, the biologically active agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Creston®), and simvastatin (Zocor®, Lipex®). Several actives comprising a combination of a statin and another agent, such as ezetimbe/simvastatin (Vytorin®), are also suitable.

In some embodiments of the invention, the biologically active agent comprises a cell selected from the group comprising human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogeneic cells, allogeneic cells, and post-natal stem cells.

In some embodiments of the invention, the biologically active agent comprises a growth factor selected from the group comprising a fibroblast growth factor-2 (FGF-2), platelet derived growth factor (PDGF), epidermal growth factor (EGF), transforming growth factor-$\alpha$ (TGF-$\alpha$), transforming growth factor beta (TGF-$\beta$), vascular epithelial growth factor (VEGF), hepatocyte growth factor (HGF), insulin-like growth factor (IGF), nerve growth factor (NGF), platelet derived growth factor (PDGF), tumor necrosis factor $\alpha$ (TNA-$\alpha$), and placental growth factor (PLGF).

In some embodiments, the biologically active agent comprises a growth factor selected from the group comprising FGF-2, TGF-$\beta$ and VEGF.

In some embodiments, the ECM (and/or an expandable ECM member formed therefrom) comprises a pharmacological agent (or composition), i.e. an agent or composition that is capable of producing a desired biological effect in vivo, e.g., stimulation or suppression of apoptosis, stimulation or suppression of an immune response, etc.

According to the invention, the pharmacological agent or composition can comprise, without limitation, antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

As also indicated above, in some embodiments of the invention, the expandable construct further comprises an integral, internal support (or anchoring) structure.

According to the invention, the support structure provides several significant advantages to the expandable construct and, hence, perivalvular leak sealing apparatus, including, without limitation, enhancing the structural integrity of the expandable construct and, hence, perivalvular leak sealing apparatus, maintaining the positioning of the expandable construct proximate perivalvular leaks, and enhancing the engagement of the expandable construct to cardiovascular tissue and, hence, cardiovascular structures.

As discussed in detail below, in some embodiments of the invention, the support structure comprises a reinforcing ring or band. According to the invention, the support structure can be positioned on or in the expandable construct.

Preferably, the support structure comprises a biocompatible material, such as, without limitation, Nitinol® and stainless steel.

As discussed in detail in U.S. Pat. No. 9,737,399, which is incorporated by reference herein, a Nitinol® support structure is also capable of transitioning from a pre-deployment configuration, such as shown in FIGS. 2A and 2B, to an expanded post-deployment configuration, such as shown in FIGS. 3A and 3B, alone or when employed in conjunction with an expandable construct.

In a preferred embodiment of the invention, the support structure comprises a biocompatible and biodegradable material.

In some embodiments, the support structure thus comprises magnesium or an alloy thereof.

In some embodiments of the invention, the magnesium and/or magnesium alloy support structure includes an immunomodulating compound coating that suppresses acute immune responses, while up regulating chronic immune response (i.e. tissue reconstruction).

In some embodiments, the immunomodulating compound comprises a polysaccharide, including, without limitation, GAGs, dextrans, alginate and chitosan.

In some embodiments, immunomodulating compound comprises a high molecular weight hyaluronic acid (HMW-HA).

In some embodiments, the support structure comprises porous polyurethane-urea (Artelon™).

In some embodiments, the support structure comprises poly(glycerol sebacate) (PGS).

In some embodiments, the expandable construct and, hence, perivalvular leak sealing apparatus comprises a poly(glycerol sebacate) (PGS) outer coating. According to the invention, the PGS outer coating provides adhesion properties to the expandable construct and, hence, perivalvular leak sealing apparatus, and, thus, facilitates adhesion of the expandable construct and, hence, perivalvular leak sealing apparatus to cardiovascular tissue.

In some embodiments, the support structure comprises cross-linked ECM.

In some embodiments, the support structure comprises a microneedle support structure, such as disclosed in Co-Pending U.S. application Ser. No. 13/686,131, now U.S. Pat. No. 8,778,012, which is expressly incorporated by reference herein. As set forth in U.S. application Ser. No. 13/686,131, the microneedle support structure includes a plurality of biodegradable microneedles or barbs that are configured to engage biological tissue; particularly, cardiovascular tissue.

In some embodiments, the microneedles comprise drug-eluting members that facilitate the direct administration of a biologically active or pharmacological agent to host tissue, e.g. cardiovascular tissue.

Referring now to FIGS. 2A, 2B, 3A, 3B, 4 and 5, a first embodiment of a perivalvular leak sealing apparatus of the invention (denoted "20") will be described in detail.

Figure 1B:
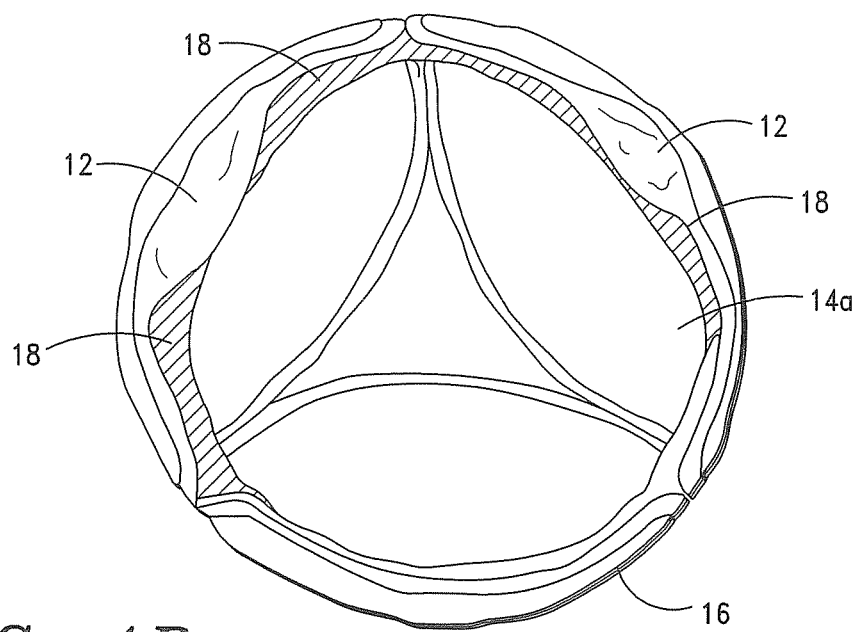

Referring first to FIG. 1B, as stated above, typically, a replacement valve 14a, such as the prosthetic valves disclosed in Co-Pending U.S. application Ser. No. 13/782,024, now U.S. Pat. No. 9,044,319, and Ser. No. 13/804,683, is placed over native (and often calcified) valve leaflets 12. The valve leaflets 12 are thus wedged between the replacement valve 14a and the vessel 16, which can, and often will, result in gaps 18 between the valve 14a and vessel 16, which can, and often will, lead to one or more perivalvular leaks.

According to the invention, the perivalvular leak sealing apparatus of the invention can be readily positioned in a valve, such as valve 14a, and/or, as discussed further below, between a valve, such as valve 14a, and a cardiovascular vessel or structure, such as vessel 16, proximate gaps 18 to seal any perivalvular leaks present proximate thereto.

As set forth in detail in U.S. Pat. No. 9,737,557, in some embodiments of the invention, the perivalvular leak sealing apparatus of the invention comprises a biocompatible, expandable construct that is configured to be positioned in a valve.

Figure 4:
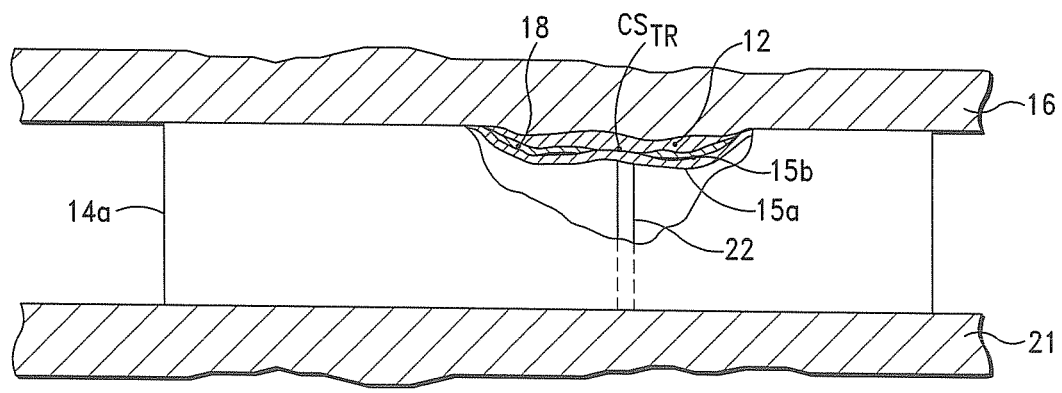
FIG. 4 is a side plan, partial sectional view of the perivalvular leak sealing apparatus shown in FIG. 3A positioned in a valve disposed in a cardiovascular vessel presenting a perivalvular leak, in accordance with the invention.
Figure 5:
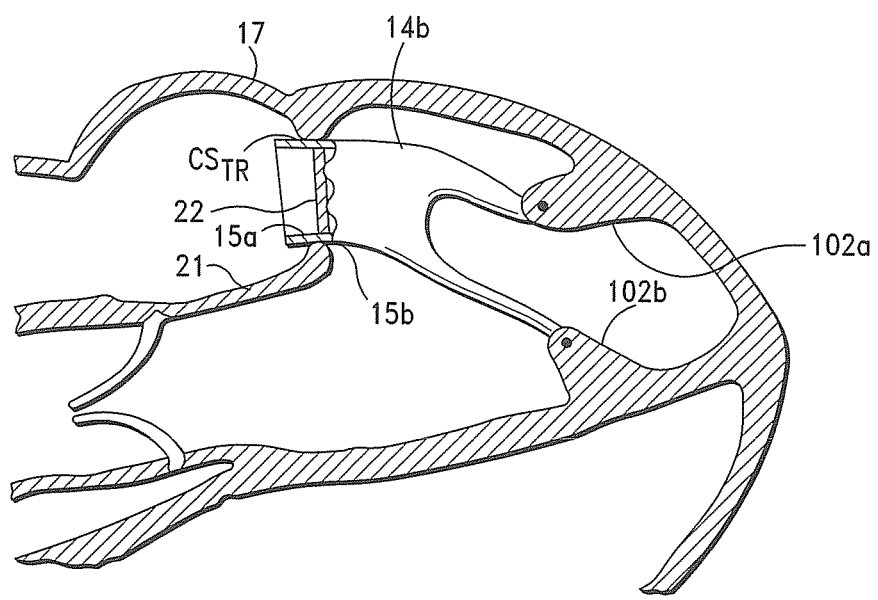
FIG. 5 is an illustration showing the perivalvular leak sealing apparatus shown in FIG. 3A positioned in a valve disposed in a cardiovascular structure presenting a perivalvular leak, in accordance with the invention.

Referring to FIGS. 2A, 2B, 3A, 3B, 4 and 5, according to the invention, the expandable construct (or member) 22 is preferably capable of transitioning from a pre-deployment configuration (as shown in FIGS. 2A and 2B), wherein the expandable construct 22 is capable of being positioned at an interior valve region 15a of a valve 14a, as illustrated in FIG. 4, (and valve 14b) when the valve 14a (and valve 14b) is disposed in a cardiovascular vessel 16 (as shown in FIG. 4) or structure 17 (as shown in FIG. 5), to a post-deployment expanded configuration (as shown in FIGS. 3A and 3B), wherein, when the expandable construct 22 is disposed at the interior valve region 15a, the valve outer surface or region 15b proximate the interior valve region 15a is placed in intimate contact with host cardiovascular tissue 21 of the cardiovascular vessel 16 or structure 17 (or a valve leaflet 12, as shown in FIG. 1B) at a cardiovascular structure target region (denoted "$CS_{TR}$") and seals perivalvular leaks present proximate thereto.

Figure 9:
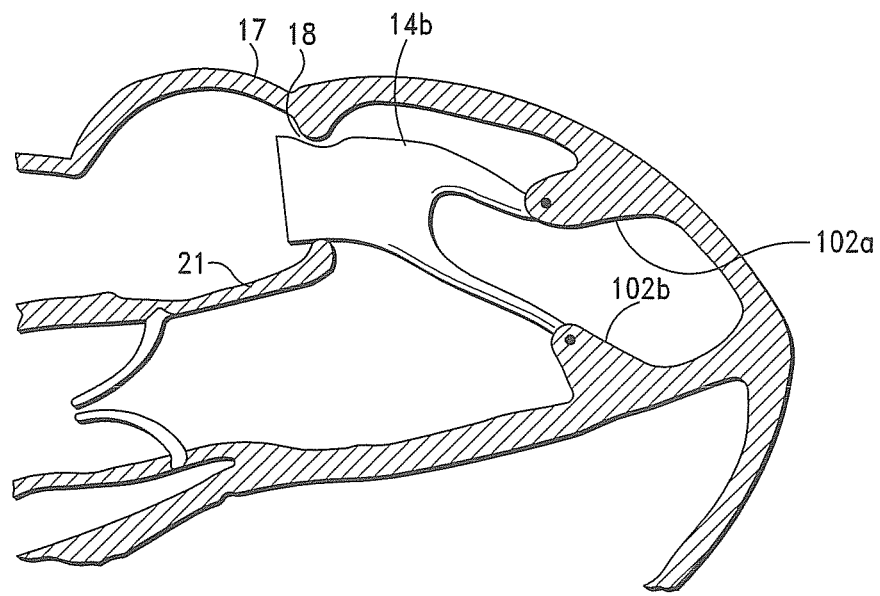
FIG. 9 is an illustration of a valve disposed in a cardiovascular structure presenting a perivalvular leak.
Figure 10:
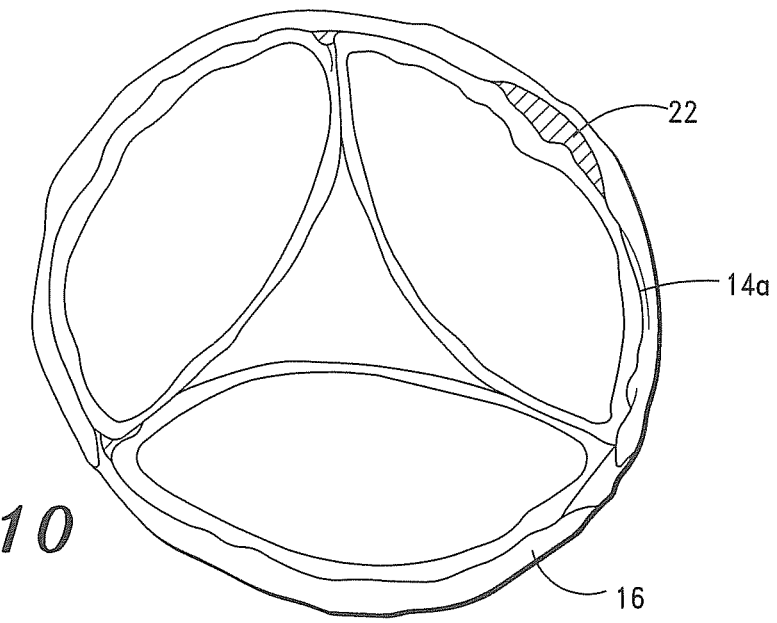
FIG. 10 is an illustration of a replacement valve disposed in a cardiovascular vessel presenting a perivalvular leak.
Figure 11:
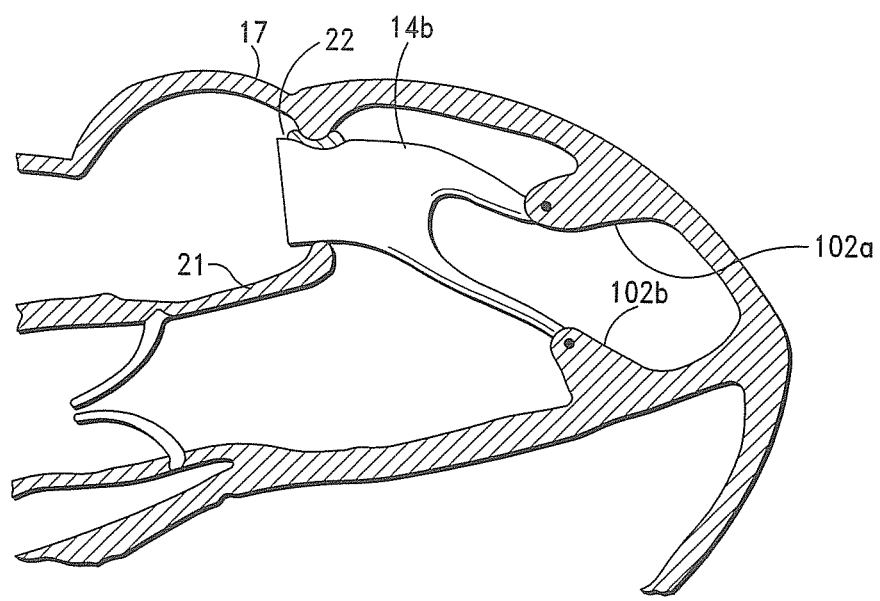
FIG. 11 is an illustration of another embodiment of a perivalvular leak sealing apparatus disposed proximate the perivalvular leak shown in FIG. 9.

As discussed in detail below, in some embodiments of the invention, the expandable construct 22 is also capable of being disposed in a gap 18 between the valve 14a (and valve 14b) and a cardiovascular vessel or structure 17 when the valve 14a (and valve 14b) is disposed in the cardiovascular vessel or structure 17, as shown in FIGS. 9-11, wherein the expandable construct 22 seals the perivalvular leak proximate the gap 18.

According to the invention, the expandable construct 22 can thus comprise various shapes, widths and lengths to accommodate placement within various sizes of valves and gaps between the valve outer surface region and a vessel wall and/or valve structure, e.g., valve annulus region.

In some embodiments, such as illustrated in FIGS. 2A, 2B, 3A and 3B, the expandable construct 22 has a substantially circular post-deployment configuration.

In some embodiments, the expandable member 22 comprises a 2°-10° arcuate member that is adapted to seal perivalvular leaks between the valve outer surface region and vessel wall and/or valve annulus region, such as shown in FIG. 11.

According to the invention, the expandable construct 22 can also comprise various biocompatible materials, including any of the aforementioned biocompatible materials.

In a preferred embodiment, the expandable construct 22 comprises a biocompatible, biodegradable and remodelable material; preferably, ECM derived from one of the aforementioned mammalian tissue sources, including, without limitation, SIS, UBS, SS, epithelium of mesodermal origin, i.e. mesothelial tissue, placental tissue, and cardiac tissue, e.g., pericardium and/or myocardium tissue, and combinations thereof.

In a preferred embodiment, the ECM comprises acellular ECM.

In some embodiments of the invention, the expandable ECM construct (or expandable remodelable construct) 22 has a sponge-like structure, i.e. a flexible, porous structure that is capable of absorbing a bodily fluid and expanding when exposed thereto.

As indicated above, in some embodiments of the invention, wherein the expandable construct 22 comprises acellular ECM derived from a mammalian tissue source, the perivalvular leak sealing apparatus thus comprises a two-stage perivalvular leak sealing structure comprising a physiomechanical leak abatement component and a biological leak abatement component, the two-stage perivalvular leak sealing structure, when disposed proximate a perivalvular leak, such as a gap between a prosthetic tissue valve and cardiovascular structure, being adapted to absorb a bodily fluid and expand, wherein the expandable remodelable construct 22 is positioned in intimate contact with cardiovascular tissue proximate the perivalvular leak and abates the perivalvular leak during a first leak sealing stage (i.e. a physiomechanical leak abatement component), and after a first period of time the expandable remodelable construct 22 remodels and induces remodeling of the cardiovascular tissue and regeneration of new cardiovascular tissue proximate the perivalvular leak, wherein the expandable remodelable construct 22 further abates the perivalvular leak during a second sealing stage (i.e. a biological leak abatement component).

In some embodiments, the ECM (and/or expandable ECM construct 22 formed therefrom) comprises at least one supplemental biologically active agent (or composition).

In some embodiments of the invention, the biologically active agent comprises one or more of the aforementioned hemostatic agents or compositions, including, without limitations, thrombin and fibrinogen.

In some embodiments of the invention, the biologically active agent comprises one or more of the aforementioned cells, including, without limitation, human embryonic stem cells, mesenchymal stem cells, parenchymal cells, epithelial cells and endothelial cells.

In some embodiments of the invention, the biologically active agent comprises one or more of the aforementioned growth factors, including, without limitation, FGF-2, TGF-β and VEGF.

In some embodiments of the invention, the biologically active agent comprises one or more of the aforementioned pharmacological agents or compositions, including, without limitation, an antibiotic, anti-viral agent, and anti-inflammatory.

Figure 6:
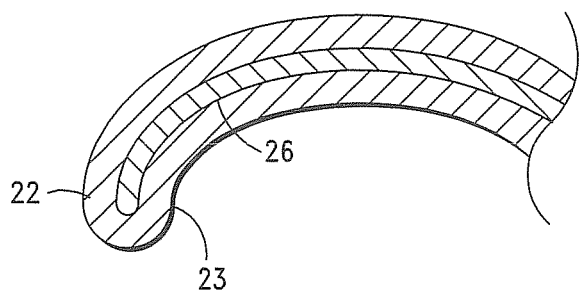
FIG. 6 is a partial side plan sectional view of one embodiment of a perivalvular leak sealing apparatus having a support structure disposed within an expandable base member, in accordance with the invention.
Figure 7:
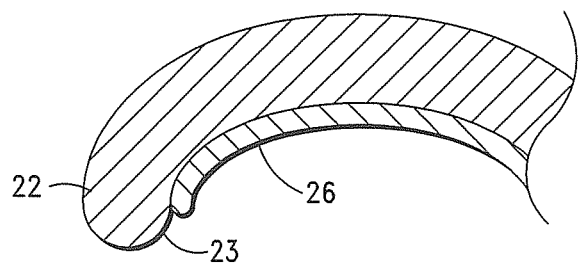
FIG. 7 is a partial side plan sectional view of another embodiment of a perivalvular leak sealing apparatus having a support structure disposed proximate the outer surface of an expandable base member, in accordance with the invention.

Referring now to FIGS. 6-7, there are shown further embodiments of the expandable construct 22, wherein the expandable construct 22 includes an integral, internal support (or anchoring) structure 26. As indicated above, the support structure 26 provides several significant advantages to the expandable construct 22 and, hence, perivalvular leak sealing apparatus, including, without limitation, enhancing the structural integrity of the expandable construct 22 and, hence, perivalvular leak sealing apparatus, maintaining the positioning of the expandable construct 22 proximate perivalvular leaks, and enhancing the engagement of the expandable construct 22 to cardiovascular tissue and, hence, cardiovascular structures.

As illustrated in FIGS. 6-7, in some embodiments, the support structure 26 comprises a reinforcing ring or band.

In some embodiments, the support structure 26 is disposed in the expandable structure 22, as shown in FIG. 6. In some embodiments, the support structure 26 is disposed proximate the outer surface 23 of the expandable structure 22, as shown in FIG. 7.

In some embodiments of the invention, the support structure 26 is similarly capable of transitioning from a pre-deployment configuration, such as shown in FIG. 2A, to a post-deployment configuration, such as shown in FIG. 3A, wherein, the support structure 26 (and, hence, expandable structure 22 associated therewith) positions a valve outer surface or region 15b in intimate contact with host cardiovascular tissue 21 of a cardiovascular vessel 16 or structure 17 proximate a cardiovascular leak, such as shown in FIGS. 4 and 5, or, in some embodiments, cardiovascular tissue in a gap 18 between a prosthetic valve, i.e. 14a, 14b and a cardiovascular vessel 16 or structure presenting a perivalvular leak, as shown in FIGS. 9-11.

According to the invention, the support structure 26 can comprise any of the aforementioned biocompatible metals, including, Nitinol®, stainless steel and cobalt-chrome nickel alloys.

The support member 26 can also comprise a polymeric material, such as disclosed in U.S. Pat. No. 9,737,399.

In a preferred embodiment of the invention, the support structure 26 comprises a biocompatible and biodegradable material.

In some embodiments, the support member thus comprises magnesium or an alloy thereof.

In some embodiments of the invention, the magnesium and/or magnesium alloy support structure includes one of the aforementioned immunomodulating compound coatings that suppresses acute immune responses, while up regulating chronic immune response (i.e. tissue reconstruction).

In some embodiments, the support structure 26 comprises poly(glycerol sebacate) (PGS). Further details regarding PGS and various compositions thereof (which are referenced to therein as ECM-mimicking compositions) are set forth in U.S. application Ser. No. 15/386,610, which is expressly incorporated by reference herein.

In some embodiments, the expandable structure 22 and, hence, perivalvular leak sealing apparatus comprises a PGS outer coating. As indicated above, the PGS outer coating provides adhesion properties to the expandable structure 22 and, hence, perivalvular leak sealing apparatus, and, thus, facilitates adhesion of the expandable structure 22 and, hence, perivalvular leak sealing apparatus to cardiovascular tissue.

Figure 8:
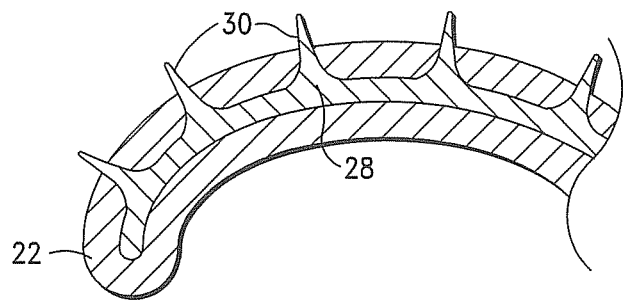
FIG. 8 is a partial side plan sectional view of another embodiment of a perivalvular leak sealing apparatus having a microneedle support structure, in accordance with the invention.

As indicated above and shown in FIG. 8, in some embodiments, the support structure comprises a microneedle support structure 28 having a plurality of microneedles (or barbs) 30 that are configured to engage biological tissue; particularly, cardiovascular tissue and, hence, cardiovascular structures.

In some embodiments, the support structure comprises a microneedle support structure 28 having a plurality of biodegradable microneedles (or barbs) 30.

Thus, in some embodiments of the invention, there is provided a perivalvular leak sealing apparatus or system comprising a biocompatible and biodegradable construct comprising ECM derived from a mammalian tissue source; particularly, SIS tissue, which is preferably subjected to a decellularization process comprising subjecting the tissue to incubation in 0.1-0.2 vol. % peracetic acid for a period of time in the range of approx. 1-2 hours, wherein the processed ECM is rendered acellular and exhibits a flexible, porous, expandable structure that expands upon exposure to and absorption of a bodily fluid.

In some embodiments of the invention, there is provided a perivalvular leak sealing apparatus or system comprising a biocompatible and biodegradable construct comprising a remodelable base construct and an integral, internal support structure, the remodelable base construct comprising acellular ECM derived from a mammalian tissue source; particularly, SIS tissue, the acellular ECM comprising a flexible, porous, expandable structure that expands upon exposure to and absorption of a bodily fluid, the internal support structure comprising poly(glycerol sebacate) (PGS).

In some embodiments, the expandable, remodelable base construct and, hence, perivalvular leak sealing apparatus further comprises an outer PGS coating.

In some embodiments of the invention, there is also provided a perivalvular leak sealing apparatus or system comprising a biocompatible and biodegradable construct comprising a remodelable base construct and an integral, internal support structure, the remodelable base construct comprising acellular ECM derived from a mammalian tissue source; particularly, SIS tissue, the acellular ECM comprising a flexible, porous, expandable structure that expands upon exposure to and absorption of a bodily fluid, the internal support structure comprising magnesium or an alloy thereof.

In some embodiments, the expandable, remodelable base construct and, hence, perivalvular leak sealing apparatus similarly includes an outer PGS coating.

In some embodiments of the invention, there is also provided a perivalvular leak sealing apparatus or system comprising a two-stage perivalvular leak sealing structure comprising a physiomechanical leak abatement component and a biological leak abatement component, the two-stage leak abatement structure comprising an expandable, remodelable base construct comprising acellular ECM derived from a mammalian tissue source, the acellular ECM and, hence, remodelable construct formed therefrom, comprising a flexible, porous structure adapted to expand upon exposure to and absorption of a bodily fluid, wherein, when the two-stage perivalvular leak sealing structure is disposed proximate a perivalvular leak, such as a gap between a prosthetic tissue valve and cardiovascular structure, and absorbs a bodily fluid, the expandable, remodelable base construct expands and is positioned in intimate contact with cardiovascular tissue proximate the perivalvular leak, wherein the perivalvular leak sealing apparatus abates the perivalvular leak during a first leak sealing stage (i.e. a physiomechanical leak abatement component), and after a first period of time the expandable, remodelable base construct remodels and induces remodeling of the cardiovascular tissue and regeneration of new cardiovascular tissue proximate the perivalvular leak, wherein the perivalvular leak sealing apparatus further abates the perivalvular leak during a second sealing stage (i.e. a biological leak abatement component).

As will readily be appreciated by one having ordinary skill in the art, the present invention provides numerous advantages. Among the advantages are the following:

The provision of a perivalvular leak sealing apparatus that can be readily employed to effectively seal perivalvular leaks.

The provision of a two-stage perivalvular leak sealing apparatus that can be readily employed to effectively seal perivalvular leaks.

The provision of perivalvular leak sealing apparatus that induce cell proliferation, bioremodeling and regeneration of new cardiovascular tissue and tissue structures with site-specific structural and functional properties.

The provision of perivalvular leak sealing apparatus that can administer a biologically active agent to cardiovascular tissue and, thereby, produce a desired biological and/or therapeutic effect.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A perivalvular leak sealing apparatus, consisting of:
a leak sealing structure consisting of a radially self-expanding base member and an integral, internal reinforcing ring, said reinforcing ring encased in said base member,
said base member consisting of acellular extracellular matrix (ECM) derived from small intestine submucosa (SIS) tissue, said acellular ECM consisting of a self-expanding, remodelable, porous, absorbent sponge-like structure adapted to receive and absorb a bodily fluid, and expand upon said receipt and absorption of said bodily fluid,
said internal reinforcing ring consisting of poly(glycerol sebacate)(PGS),
said acellular ECM sponge-like structure and said PGS internal support structure adapted to induce remodeling of cardiovascular tissue, when disposed proximate to said cardiovascular tissue,
said acellular ECM sponge-like structure further adapted to induce regeneration of new cardiovascular tissue, when in said proximate position with said cardiovascular tissue,
said leak sealing structure, upon absorption of a first bodily fluid by said base member, adapted to expand and transition from a pre-deployment configuration, wherein said leak sealing structure is capable of being positioned proximate a perivalvular leak proximate a cardiovascular structure, to a post-deployment configuration, wherein said base member of said leak sealing structure is positioned in intimate contact with cardiovascular tissue proximate said perivalvular leak and abates said perivalvular leak during a first leak sealing stage, and said acellular ECM sponge-like structure and said PGS internal support structure induce remodeling of said cardiovascular tissue proximate said perivalvular leak, and said acellular ECM sponge-like structure induces regeneration of new cardiovascular tissue proximate said perivalvular leak, wherein said leak sealing structure further abates said perivalvular leak during a second leak sealing stage.

2. A perivalvular leak sealing apparatus, comprising:
a two-stage leak sealing structure comprising a physiomechanical leak abatement component and a biological leak abatement component,
said leak sealing structure comprising a radially self-expanding base member and an integral, internal support structure,
said base member comprising acellular extracellular matrix (ECM) derived from small intestine submucosa (SIS) tissue, said acellular ECM being decellularized by a decellularization process comprising incubation of ECM derived from said SIS tissue in a decellularization agent for a period of time in the range of 0.1-168 hours, wherein said acellular ECM comprises a self-expanding, remodelable, porous sponge-like structure, said acellular ECM adapted to remodel and induce remodeling and regeneration of cardiovascular tissue, when disposed proximate to said cardiovascular tissue, said internal support structure comprising a microneedle support structure, said microneedle support structure comprising a plurality of biodegradable microneedles adapted to engage mammalian tissue, said leak sealing structure, upon absorption of a bodily fluid, being adapted to expand and transition from a pre-deployment configuration, wherein said leak sealing structure is capable of being positioned proximate a perivalvular leak, to an expanded post-deployment expanded configuration, wherein said leak sealing structure is positioned in intimate contact with cardiovascular tissue proximate said perivalvular leak, said plurality of microneedles of said microneedle support structure engage said cardiovascular tissue and said leak sealing structure abates said perivalvular leak during a first leak sealing stage, and said leak sealing structure induces remodeling of said cardiovascular tissue proximate said perivalvular leak and regeneration of new cardiovascular tissue and further abates said perivalvular leak during a second leak sealing stage, said first leak sealing stage defining said physiomechanical leak abatement component, said second leak sealing stage defining said biological leak abatement component.

3. The apparatus of claim 2, wherein said decellularization agent is selected from the group consisting of deoxycholic acid, sodium dodecyl sulfate (SDS), triton X-100, 3-[(3-cholamidopropyl) dimethylammonio]-1-propanesulfonate (CHAPS), peracetic acid (PAA), hydrogen peroxide ($H_2O_2$), acetic acid (AcA), trifluoroacetic acid (TFA), and mixtures thereof.

4. The apparatus of claim 2, wherein said acellular ECM further comprises a supplemental biologically active agent.

5. The apparatus of claim 4, wherein said supplemental biologically active agent comprises a hemostatic agent selected from the group consisting of thrombin and fibrinogen.

6. The apparatus of claim 4, wherein said supplemental biologically active agent comprises a growth factor selected from the group consisting of basic fibroblast growth factor (bFGF), transforming growth factor beta (TGF-β), and vascular epithelial growth factor (VEGF).

* * * * *